(12) United States Patent
Morizane et al.

(10) Patent No.: US 6,822,090 B2
(45) Date of Patent: Nov. 23, 2004

(54) PROCESS FOR THE PREPARATION OF CYTIDINE DERIVATIVES

(75) Inventors: Kunihiko Morizane, Chiba (JP); Hiroharu Tanikawa, Chiba (JP); Toshiyuki Kouno, Chiba (JP); Hironori Komatsu, Chiba (JP); Nobuyuki Fukazawa, Tokyo (JP)

(73) Assignee: Mitsui Chemicals, Inc., Tokyo (JP)

( * ) Notice: Subject to any disclaimer, the term of this patent is extended or adjusted under 35 U.S.C. 154(b) by 62 days.

(21) Appl. No.: 10/009,805

(22) PCT Filed: Apr. 13, 2001

(86) PCT No.: PCT/JP01/03191

§ 371 (c)(1), (2), (4) Date: Mar. 6, 2002

(87) PCT Pub. No.: WO01/79248

PCT Pub. Date: Oct. 25, 2001

(65) Prior Publication Data

US 2003/0032797 A1 Feb. 13, 2003

(30) Foreign Application Priority Data

Apr. 13, 2000 (JP) .................................. 2000-112361

(51) Int. Cl.[7] ..................... C07H 19/067; C07H 19/073
(52) U.S. Cl. .................................... 536/28.53; 536/28.5
(58) Field of Search ............................... 536/28.5, 28.53

(56) References Cited

U.S. PATENT DOCUMENTS 5,610,292 A * 3/1997 Karimian .................. 536/55.3

5,631,239 A 5/1997 Lin et al.

FOREIGN PATENT DOCUMENTS

| JP | 1-143892 | 6/1989 |
|---|---|---|
| JP | 6-329560 | 11/1994 |
| JP | 2000-327693 | 11/2000 |

OTHER PUBLICATIONS

Awano, H. et al "Synthesis andAntiviral Activity of 5–Substituted (2'S)–2'–Deoxy–2'C–Methylcytidines and –Uridines", Arch. Pharm. Pharm. Med. Chem. 1996, 329, 66–72).*

W.L. Sung, "Synthesis of 4–(1,2, 4–Triazol–1–yl)pyrimidin–2(1H)–one Ribonucleotide and Its Application in Synthesis of Oligoribonucleotides," *J. Org. Chem.*, 1982, pp 3623–3628, 47, American Chemical Society, USA.

H. Awano et al., "Synthesis and Antiviral Activity of 5–Substituted (2'S)–2'–Deoxy–2'–C–Methylcytidines and –uridines," Nucleosides and Nucleotides, Part 144, *Arch. Pharm, Pharm. Med. Chem.*, 1996, pp 66–72, VCH Verlagsgesellschaft mbH, Weinheim, Germany.

* cited by examiner

*Primary Examiner*—James O. Wilson
*Assistant Examiner*—Ganapathy Krishnan
(74) *Attorney, Agent, or Firm*—Burns, Doane, Swecker & Mathis, L.L.P.

(57) ABSTRACT

An efficient method for producing cytidine derivatives that took away the previous drawbacks by efficiently synthesizing cytidine derivatives by utilizing a tertiary amine can be provided.

11 Claims, No Drawings

PROCESS FOR THE PREPARATION OF CYTIDINE DERIVATIVES

TECHNICAL FIELD

The present invention relates to a method for producing cytidine derivatives. The cytidine derivatives are useful not only as pharmaceuticals, such as antitumor agents and antiviral agents, and agricultural chemicals, but also as a raw material of antisense DNAs that are being developed now.

BACKGROUND ART

Examples of the known method for producing cytidine derivatives are as follows.

(1) The method in which 5'-O-(dimethoxytrityl)uridine derivatives are condensed with 1,2,4-triazole to give 1-[5'-O-(dimethoxytrityl)-β-D-ribofuranosyl]-4-(1,2,4-tri azol-1-yl)pyrimidin-2-(1H) -one derivatives, which are then reacted with an amine in dioxane solvent to yield 5'-O-(dimethoxytrityl)cytidine derivatives (Journal of Organic Chemistry, 47, 3623 (1982)).

(2) The method in which 2'-deoxy-2'-methyluridine derivatives are reacted with 4-(N,N-dimethylamino) pyridine (thereinafter referred to as DMAP) to give 4-[4-(N,N-dimethylamino)pyridinium] derivatives, which are then treated with 28% NH₄OH to yield 2'-deoxy-2'-methylcytidine derivatives (Arch. Pharm., 329, 66 (1996)).

As for the above methods, the method (1) using 1,2,4-triazole is unsuitable for mass production, since the reaction for the synthesis of 4-(1,2,4-triazol-1-yl)pyrimidin-2-(1H)-one derivatives is extremely slow and time-consuming, and the extraction of the product is required, thereby taking a lot of time and effort; and the method (2) via 4-[4-(dimethylamino)pyridinium] derivatives is also unsuitable for mass production, since the reaction is extremely slow and time-consuming, and, if less than 2.0 equivalents of DMAP is used based on the reaction substrate, then the unchanged substrates remain and the manipulation to separate them from the product becomes necessary, resulting in an increase in the number of processes, as described in the comparative examples later.

DISCLOSURE OF INVENTION

Thus, any efficient methods for producing cytidine derivatives capable of supplying them in large quantities have been absent previously. The present invention provides a method for producing cytidine derivatives efficiently.

The inventors have intensively investigated in order to solve the above problems, and then found that uridine derivatives can be reacted with a tertiary amine and a dehydrating reactant in the presence of a deacidifying agent, followed by ammonia, or a primary or secondary amine to yield cytidine derivatives in a short period of time by means of an easy manipulation. That is, the reaction time, which was long in the conventional methods, was largely reduced. Furthermore, it was found that the tertiary amine to be used could be reduced to nearly the same mole based on the uridine derivative, and then the present invention was completed.

Accordingly, the method for producing cytidine derivatives of the present invention is the method, characterized in that a uridine derivative represented by formula (1):

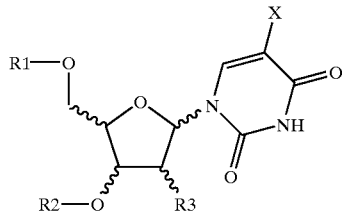

(1)

wherein, X represents a hydrogen atom, a halogen atom, an alkyl group having 1 to 4 carbon atoms, an alkyl group having 1 to 4 carbon atoms substituted with a halogen atom(s), or an alkenyl group having 2 to 4 carbon atoms, and R1 and R2 each independently represent either a hydrogen atom or a hydroxyl-protecting group, and R3 represents a hydrogen atom, a halogen atom, a hydroxyl group, an alkyl group having 1 to 4 carbon atoms, a cyano group, an alkenyl group, an alkynyl group, an alkoxy group having 1 to 4 carbon atoms, a hydroxyl group substituted with a hydroxyl-protecting group, is reacted with a tertiary amine and dehydrating reactant, followed by ammonia, or a primary or secondary amine represented by formula (2):

HNR4R5 (2)

wherein, R4 and R5 each independently represent a hydrogen atom, an alkyl group having 1 to 4 carbon atoms, a cycloalkyl group having 5 to 8 carbon atoms, an alkyl group having 1 to 4 carbon atoms substituted with a halogen atom(s), or an alkenyl group having 2 to 4 carbon atoms, or R4 and R5 may be linked together to form a ring, for producing a cytidine derivative represented by formula (3):

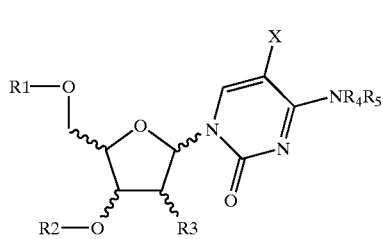

(3)

wherein, X, R1, R2, R3, R4 and R5 are as defined above.

Preferably, in the above formulas, examples of the hydroxyl-protecting groups, i.e. R1 and R2, include an aliphatic acyl group having 1 to 4 carbon atoms, an aromatic acyl group, an aromatic acyl group substituted with an alkyl group(s) having 1 to 4 carbon atoms, an aromatic acyl group substituted with a halogen atom(s), an aromatic acyl group substituted with an alkoxy group(s) having 1 to 4 carbon atoms, or a trialkylsilyl group, R3 may be a hydrogen atom, an alkoxy group having 1 to 4 carbon atoms, an aliphatic alkyloxy group having 1 to 4 carbon atoms substituted with an alkoxy group(s) having 1 to 4 carbon atoms, an aliphatic acyloxy group having 1 to 4 carbon atoms, an aromatic acyloxy group, an aromatic acyloxy group substituted with an alkyl group(s) having 1 to 4 carbon atoms, an aromatic acyloxy group substituted with a halogen atom(s), or an aromatic acyloxy group substituted with an alkoxy group(s) having 1 to 4 carbon atoms.

The preferred combination of X and R3 in the above formulas (1) and (3) includes the combination in which X represents a hydrogen atom or a methyl group, and R3 is a hydrogen atom, a methoxy group, or a methoxyethyl group.

Examples of the above tertiary amine include an alicyclic amine represented by formula (4):

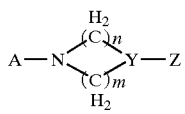
(4)

wherein, n and m each independently represent an integer of 1 to 4, Y represents hydrogen atom, carbon atom, nitrogen atom, oxygen atom, or sulfur atom, Z represents a hydrogen atom, an alkyl group having 1 to 4 carbon atoms, an alkyl group having 1 to 4 carbon atoms substituted with a halogen atom(s), an alkenyl group having 2 to 4 carbon atoms, or Z may be linked to A to form a ring, A represents an alkyl group having 1 to 4 carbon atoms, an alkyl group having 1 to 4 carbon atoms substituted with a halogen atom(s), an alkenyl group having 2 to 4 carbon atoms, or A may be linked to Z to form a ring; and an aliphatic amine represented by formula (6):

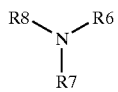
(6)

wherein, R6, R7 and R8 each independently represent an alkyl group having 1 to 4 carbon atoms, a cycloalkyl group having 5 to 8 carbon atoms, an alkyl group having 1 to 4 carbon atoms substituted with a halogen atom(s), or an alkenyl group having 2 to 4 carbon atoms.

The specific examples of the tertiary amine include N-methylpiperidine, N-methylmorpholine, 1,4-diazabicyclo[2.2.2]octane, N,N'-dimethylpiperazine, and trimethylamine.

On the other hand, the method for producing cytidine derivatives of the present invention can possess the reaction route capable of obtaining a cytidine derivative represented by formula (5):

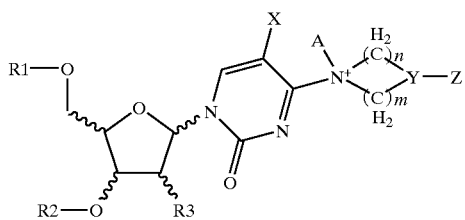
(5)

wherein, X, R1, R2, R3, n, m, A, Y and Z are as defined above, as a reaction intermediate, in reacting the uridine derivative with the tertiary amine and the dehydrating reactant.

Examples of the dehydrating reactants in the above reaction include acid halides or acid anhydrides, and in this case, the above reaction is preferably conducted in the presence of a deacidifying agent. The specific examples of the above dehydrating reactant include p-toluenesulfonyl chloride.

The molar ratio of the above tertiary amine to the uridine derivative represented by formula (1) may be, for example, 1.2 or less.

A cytidine derivative represented by formula (5):

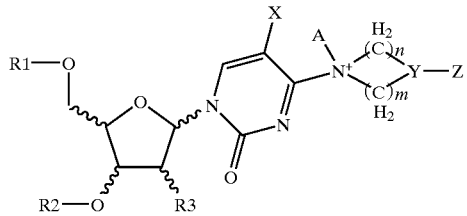
(5)

wherein, X, R1, R2, R3, n, m, A, Y and Z are as defined above, or salt thereof is a novel compound, and included in the present invention. The compounds of the above formula (5) include one, where X represents a hydrogen atom or a methyl group, R1 and R2 are a hydrogen atom or a hydroxyl-protecting group, R3 is a hydrogen atom, a methoxy group, a methoxyethyloxy group, n and m are 2, A is a methyl group, and Y is a methylene group or an oxygen atom.

Another aspect of the method for producing cytidine derivatives according to the present invention is the method for producing a cytidine derivative represented by formula (3):

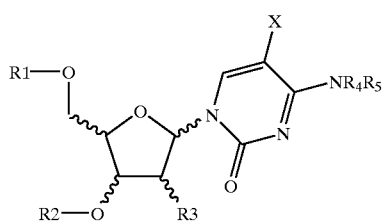
(3)

wherein, X, R1, R2, R3, R4 and R5 are as defined above, characterized in that a cytidine derivative represented by the above formula (5) or a salt thereof is reacted with ammonia, or the above primary or secondary amine.

The use of the method suitable for mass production according to the present invention made it possible to produce cytidine derivatives more efficiently as compared with the conventional methods.

Best Mode for Carrying Out the Invention

Now, the present invention will be described in detail.

X in a uridine derivative represented by formula (1) (thereinafter referred to as the uridine derivative (1)) is, but not limited to, a hydrogen atom; a halogen atom, such as a fluorine atom, a chlorine atom, a bromine atom and an iodine atom; an alkyl group, i.e. a methyl group, an ethyl group, a propyl group, a 2-propyl group, and a tertiary butyl group; an alkyl group having 1 to 4 carbon atoms substituted with a halogen atom(s), i.e. a chloromethyl group, a dichloromethyl group, and a trifluoromethyl group; an alkenyl group having 2 to 4 carbon atoms, i.e. a bromovinyl group.

R1 and R2 in the uridine derivative (1) independently represent a hydrogen atom or a hydroxyl-protecting group. Hydroxyl-protecting groups include, for example, alkyl ethers, aralkyls, acyls, carbonates, sulfonates, silyls.

Alkyl ethers, such as a methoxymethyl group, a 2-methoxyethyl group, a 1-ethoxyethyl group, a 2-methoxyethoxymethyl group, and a tetrahydropyranyl group can be used.

Aralkyls, such as a benzyl group, a 4-methoxybenzyl group, a 2-nitrobenzyl group, a trityl group, a 4-methoxytrityl group and a 4,4'-dimethoxytrityl group can be used.

Both of an aliphatic acyl group and an aromatic acyl group can be used as the acyls. Such acyl groups may have one or more substituents, such as halogen, an alkyloxy group, a nitro group, an acyl group, and an alkyl group, if necessary.

More preferably, the above acyl groups include an aliphatic acyl group, such as an acetyl group and a propionyl group, and an aromatic acyl group, such as a benzoyl group, a toluoyl group, a nitrobenzoyl group, a 4-chlorobenzoyl group, a 3-chlorobenzoyl group, a 2-chlorobenzoyl group and a 4-methoxybenzoyl group.

Carbonates, such as a methoxycarbonyl group, an ethoxycarbonyl group, a tertiary butyloxycarbonyl group, a benzyloxycarbonyl group, and a phenyloxycarbonyl group can be used.

Sulfonates, such as a p-toluenesulfonyl group, a methanesulfonyl group, a 2,4,6-trimethylphenylsulfonyl group, a and a 2,4,6-triisopropylphenylsulfonyl group can be used.

Silyls, such as a trimethylsilyl group, a triethylsilyl group, a dimethyl-tert-butylsilyl group, a diphenylmethylsilyl group, a triphenylsilyl group, and a 1,1,3,3-tetraisopropyldisiloxan-1,3-diyl group can be used.

R3 in the uridine derivative (1) includes, for example, a hydrogen atom; a halogen atom, such as a fluorine atom, a chlorine atom, a bromine atom and an iodine atom; a hydroxyl group; an alkyl group having 1 to 4 carbon atoms, i.e. a methyl group, an ethyl group, a propyl group, a 2-propyl group, and a tertiary butyl group; a cyano group; an alkenyl group, such as a bromovinyl group; an alkynyl group, such as ethynyl group; an alkoxy group having 1 to 4 carbon atoms, i.e. a methoxy group, an ethyloxy group, a n-propyloxy group, and a n-butyloxy group; or a hydroxyl group substituted with the above hydroxyl-protecting group. More preference is given to a hydrogen atom, a methoxy group, and a methoxyethyloxy group.

Examples of tertiary amines represented by formulas (4) and (6) include a trimethylamine, a triethylamine, a tripropylamine, a tri(2-propyl)amine, a tributylamine, a tri(2-butyl)amine, a tri(tert-butyl)amine, a di(2-propyl)ethylamine, a N-methylpyrrolidine, a N-methylpiperidine, a N-methylpyrrole, a N,N'-dimethylpiperazine, a 1,4-diazabicyclo[2.2.2]octane, a N-methylmorpholine, a N-methylthiomorpholine. The tertiary amines are not limited to these concrete groups, so far as the nucleophilicity of nitrogen atom is sufficient for the reaction to proceed.

Particular preference is given to trimethylamine, N-methylpyrrolidine, 1,4-diazabicyclo[2.2.2]octane, N-methylpiperidine, N-methylmorpholine, and N,N'-dimethylpiperazine.

R4 and R5 in ammonia, or a primary or secondary amine represented by formula (2) independently represent a hydrogen atom; an alkyl group having 1 to 4 carbon atoms, i.e. a methyl group, an ethyl group, a propyl group, a 2-propyl group, and a tert-butyl group; a cycloalkyl group having 5 to 8 carbon atoms, i.e. a cyclopentyl group, a cyclohexyl group, a cycloheptyl group, and a cyclooctyl group; an alkyl group having 1 to 4 carbon atoms substituted with a halogen atom(s), i.e. a chloromethyl group and a dichloromethyl group; an alkenyl group having 2 to 4 carbon atoms, such as a bromovinyl group, etc. Additionally, R4 and R5 may be linked together to form a ring, and in this case, R4(R5)N group may be, but not limited to, a pyrrolidine group or a piperidine group. Particular preference is given to ammonia and a piperidine.

Dehydrating reactants include, but not limited to, acid halides, acid anhydrides, esterifying-amidating agent, acidic catalysts and fluorinating agents.

Acid halides, such as a p-toluenesulfonyl chloride, a methanesulfonyl chloride, a 2,4,6-trimethylphenylsulfonyl chloride, a 2,4,6-triisopropylphenylsulfonyl chloride, a phosphorus oxychloride, a thionyl chloride, a 4-chlorophenyl dichlorophosphate, an oxalyl chloride, and a malonyl dichloride can be used. Acid anhydrides, such as trifluoromethanesulfonic anhydride, acetic anhydride, and trifluoroacetic anhydride can be used. Esterifying-amidating agents, for example, carbodiimides such as 1,3-dicyclohexylcarbodiimide; phosphoniums, such as bromo(tris-pyrrolidino)phosphonium hexafluorophosphate; pyridiniums, such as 2-chloro-N-methylpyridinium iodide; and azodicarboxylates, such as diethyl azodicarboxylate can be used. Acidic catalysts, such as boron trifluoride diethyl ether, tin tetrachloride, and aluminium trichloride can be used. Fluorinating agents, such as diethylaminosulfur trifluoride, cyanuric fluoride, and 1,3-dimethyl-2,2-difluoroimidazoline can be used. Preference is given to acid halide, and particular preference is given to p-toluenesulfonyl chloride.

Reaction solvents, such as ethers, such as diethyl ether, diisopropyl ether, tetrahydrofuran, and dioxane; an aliphatic hydrocarbon-type solvent, such as n-pentane, n-hexane and cyclohexane; an aromatic hydrocarbon-type solvent, such as benzene, toluene, xylene, and a halogenated benzene; a halogenated hydrocarbon-type solvent, such as dichloromethane, chloroform, and dichloroethane; or acetonitrile can be used in this reaction, but the reaction solvent was not limited to them. Particular preference is given to acetonitrile and chloroform.

The reaction of the uridine derivative (1) according to the present invention with a tertiary amine and a dehydrating reactant is carried out by adding the dehydrating reactant or a solution thereof to the solution of the uridine derivative (1) and the tertiary amine.

When the acidity within the reaction system affects the reaction, in addition to the tertiary amine, a deacidifying agent can be added. In addition to the above tertiary amine, examples of the deacidifying agent include, but are not limited to, organic bases, such as pyridine, lutidine, N,N-dimethylaniline, or inorganic bases, such as potassium carbonate, sodium carbonate, and sodium hydrogencarbonate; and ion-exchange resin. Particular preference is given to triethylamine.

The molar ratio of the tertiary amine to the uridine derivative (1) is in the range between 0.5 and 3.0, preferably in the range between 1.0 and 2.0, and more preferably 1.2.

The molar ratio of the dehydrating reactant to the uridine derivative (1) used in the reaction of the uridine derivative (1) with the tertiary amine and the dehydrating reactant is in the range between 0.5 and 5.0, preferably 1.0 to 3.0, and more preferably 2.0.

The molar ratio of the deacidifying agent, if used, to the uridine derivative (1) in the reaction of the uridine derivative (1) with a tertiary amine and dehydrating reactant is in the range between 0.5 and 5.0, preferably 1.0 to 3.0, and more preferably 2.0.

The temperature at the time when the dehydrating reactant or its solution is added to the solution of the uridine derivative (1) and tertiary amine can be in the range between −10° C. and 50° C., preferably in the range between −5° C. and 10° C.

The reaction of the uridine derivative (1) with the tertiary amine and the dehydrating reactant takes 0.5 to 27 hours, but the reaction time is preferably between 0.5 and 3 hours.

The synthesis of the cytidine derivative (3) according to the present invention is carried out by reacting the uridine derivative (1) with a tertiary amine and dehydrating reactant, followed by ammonia, or a primary or a secondary amine. The molar ratio of ammonia, or the primary or the secondary amine (2) to the uridine derivative (1) is in the range between 0.5 and 60, preferably 1.0 to 40, and more preferably 2.0 to 37.

As for the condition in the reaction with ammonia, or a primary or secondary amine after reacting the uridine derivative (1) with a tertiaryamine and a dehydrating reactant, the temperature can be in the range between −10° C. and 50° C., preferably in the range between −5° C. and 10° C., and it takes 0.5 to 10 hours to carry out this reaction, but the reaction time is preferably between 0.5 and 6hours. In this reaction, the activation of the 4-position of the uridine derivative by the dehydrating reactant firstly proceeds, and then the activated uridine derivative (1) is reacted with the tertiary amine to form the cytidine derivative represented by formula (5) or the ammonium salt represented by formula (7):

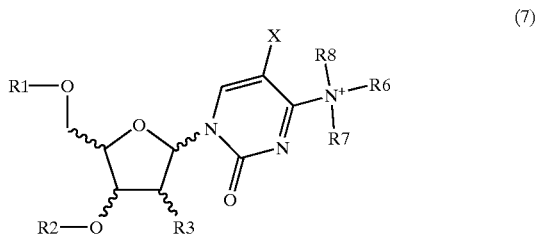

(7)

wherein, R1, R2, R3, R6, R7, R8 and X areas defined above, which are then reacted with ammonia, or a primary or secondary amine to undergo amination at the 4-position.

The cytidine derivative (3) can be also produced by treating with ammonia, or a primary or secondary amine after the isolation of the cytidine derivative (5) or (7).

The present invention, therefore, made it possible to produce the cytidine derivative (3) more efficiently.

EXAMPLES

Now, the present invention will be specifically described by the following examples, but is not limited to them.

Example 1

To 10.0 g of 3',5'-O-bis(4-chlorobenzoyl)-2'-deoxyuridine was added 50 mL of acetonitrile, 4.0 g of triethylamine, and 2.4 g (1.2 times moles based on the uridine derivative) of 1-methylpiperidine, and the resulting mixture was stirred in an ice bath. To this, the solution of 7.5 g of p-toluenesulfonyl chloride in 25 ml of acetonitrile was added dropwise over 1 hour at −1.5° C. or below −1.5° C. After the completion of addition, the mixture was stirred for 1 hour. Then, 50 mL of 28% ammonia water was added dropwise over 20 minutes at 4.5° C. or below 4.5° C. After the completion of addition, the mixture was stirred for 2.5 hours. The precipitated crystals were filtered and washed with acetonitrile to give 7.93 g of 3',5'-O-bis(4-chlorobenzoyl) -2'-deoxycytidine. Yield 79.5%.

$^1$H-NMR (400 MHz, DMSO-d6) δ 2.47–2.55 (m, 2H), 3.35 (s, 1H), 4.50–4.63 (m, 3H), 5.59–5.61 (m, 1H), 5.70 (d, J=7.6 Hz, 1H), 6.29 (t, J=7.0 Hz, 1H), 7.23 (d, J=7.8 Hz, 1H), 7.59–7.66 (m, 5H), 7.96–8.04 (m, 4H).

IR (KBr) cm$^{-1}$ 1719, 1655, 1491, 1271, 1095.

Comparative Example 1

The method given in the conventional method (2) using DMAP was examined. The results are as follows. To 0.283 g of 3',5'-O-bis(4-chlorobenzoyl)-2'-deoxyuridine was added 8.5 mL of acetonitrile, 0.221 g of p-toluenesulfonyl chloride, and 0.141 g (2.1 moles base on the uridine derivative) of DMAP, followed by adding dropwise 0.117 g of triethylamine, and the resulting mixture was stirred at room temperature for 22 hours. To this, 5.7 mL of 28% ammonia water was added and the mixture was stirred at room temperature for 2 hours, and then ice-cooled. Crystals were filtered and washed with 60% acetonitrile in water to give 0.17 g of 3',5'-O-bis(4-chlorobenzoyl)-2'-deoxycytidine. Yield 60%.

In the conventional method, thus, the reaction mixture must be stirred at room temperature for 22 hours before the addition of 28% ammonia water, although only one hours is required in the method according to the present invention, which made it possible to reduce the overall reaction time largely.

Comparative Example 2

Experiments with varying the equivalent of DMAP are described below.

To 0.2 g of 3', 5'-O-bis (4-chlorobenzoyl)-2'-deoxyuridine was added 3.0 mL of acetonitrile, 0.151 g of p-toluenesulfonyl chloride, and the equivalent shown in Table 1 of DMAP, followed by adding dropwise 80.2 mg of triethylamine, and the resulting mixture was stirred at room temperature for 30 hours. The reaction solution was analyzed by High Performance Liquid Chromatography to determine the residual rate of the reaction substrate, 3',5'-O-bis(4-chlorobenzoyl)-2'-deoxyuridine. The results are shown in Table 1.

TABLE 1

| Equivalents of DMAP to Reaction Substrate | Residual Rate of Reaction Substrate (%) |
| --- | --- |
| 2.0 | 0.0 |
| 1.2 | 11.0 |
| 0.5 | 14.4 |

As described above, if 1.2 equivalents or less of DMAP is used, the unchanged raw material remains, and the separation of it from the desired product become necessary, resulting in an increase in the number of processes. This seems to be due to the deactivation of DMAP by hydrogen chloride generated in the reaction system. On the other hand, since tertiary amines shown in the present invention are not deactivated by hydrogen chloride, no unchanged reaction substrates remains even when 1.2 equivalents of the tertiary amine is used, and the desired product can be obtained in a short time.

Example 2

To 1.0 g of 3',5'-O-bis (4-chlorobenzoyl)-2'-deoxyuridine was added 5 mL of acetonitrile, 0.40 g of triethylamine, 0.24 g (1.2 times moles based on the uridine derivative) of 1-methylpiperidine and 0.76 g of p-toluenesulfonyl chloride, and the reaction mixture was stirred in an ice bath for 2 hours. To this, 7.5 mL of a solution of ammonia in 2-propanol was added, and the mixture was stirred in an ice bath for 4 hours, and at room temperature for 1 hour. The crystals were filtered and washed with acetonitrile to give 0.54 g of 3',5'-O-bis(4-chlorobenzoyl)-2'-deoxycytidine. Yield 54%.

Example 3

To 2.0 g of 3',5'-O-bis(4-chlorobenzoyl)-2'-deoxyuridine was added 60 mL of acetonitrile, 0.81 g of triethylamine, 0.54 g (1.2 times moles based on the uridine derivative) of 1,4-diazabicyclo[2.2.2]octane and 1.5 g of p-toluenesulfonyl chloride, and the resulting mixture was stirred at room temperature for 3 hours. Ammonia gas was bubbled into the reaction mixture at room temperature for 1 hour, and the mixture was stirred in an ice bath for 30 minutes. The crystals were filtered and washed with acetonitrile to give 1.52 g of 3',5'-O-bis(4-chlorobenzoyl)-2'-deoxycytidine. Yield 75.2%.

Example 4

To 3.0 g of 3',5'-O-bis(4-chlorobenzoyl)-2'-deoxyuridine was added 30 mL of chloroform, 0.72 g of triethylamine, 0.80 g (1.2 times moles of uridine derivative) of 1,4-diazabicyclo[2.2.2]octane and 1.36g of p-toluenesulfonyl chloride, and the resulting mixture was stirred at room temperature for 30 minutes. Ammonia gas was bubbled into the reaction mixture at room temperature for 1 hour, and the mixture was stirred in an ice bath for 1 hour. After sludging by the addition of 100 mL of water and 100 mL of methanol, the crystals were filtered and washed with the mixed solution of water and methanol (1:1) to give 2.42 g of 3',5'-O-bis(4-chlorobenzoyl)-2'-deoxycytidine. Yield 80.9%.

Reference Example 1

The suspension of 5.0 g of thymine in 41.8 mL of HMDS was heated to reflux for 3 hours. After cooling, the excess HMDS was evaporated off. The residue was dissolved by the addition of 60 mL of chloroform. To this was added 11.4 g of 3,5-O-bis(4-chlorobenzoyl)-2-deoxyribofuranos-1-yl chloride (purity 85%), followed by 60 mL of chloroform, the mixture was heated at 50° C. for 4 hours with stirring. After cooling, the solution of 4.46 g of sodium hydrogen carbonate in 70 ml of water and 70 mL of methanol were added, and the mixture was stirred at room temperature for 1 hour. After the removal of the aqueous layer, the solution of 300 mg of sodium carbonate in 30 mL of water was added, and the mixture was stirred at room temperature for 10 minutes. After the separation of the layers, the solvent of the organic layer was evaporated off, and the resulting residue was purified by silica gel chromatography (chloroform:methanol =30:1) to give 10.5 g of 3',5'-O-bis(4-chlorobenzoyl) thymidine. Yield 90%.

$^1$H-NMR (400 MHz, CDCl$_3$) δ1.65 (d, J=0.7 Hz, 3H), 2.55–2.66 (m, 2H), 4.48–4.68 (m, 3H), 5.61–5.65 (m, 1H), 6.28–6.32 (m, 1H), 7.50 (d, J=0.7 Hz, 1H), 7.57–7.64 (m, 4H), 7.99–8.04 (m, 4H), 11.4 (s, 1H).

IR (KBr) cm$^{-1}$ 3193, 3067, 1720, 1680, 1593, 1488, 1276, 1013, 761.

Example 5

To the suspension of 3.00 g of 3',5'-O-bis(4-chlorobenzoyl)thymidine (a uridine derivative, where X is methyl group) in 15 mL of acetonitrile was added 0.85 mL (1.2 times moles based on the uridine derivative) of 1-methylpiperidine and 1.70 mL of triethylamine, and the resulting mixture was cooled. The solution of 2.31 g of p-toluenesulfonyl chloride in 15 ml of acetonitrile was added dropwise with keeping the temperature at 0° C. or below 0° C., and the mixture was stirred for 3 hours with keeping the temperature at 0° C. or below 0° C. With keeping the temperature at 0° C. or below 0° C., 15 ml of 28% ammonia water was added, and the mixture was stirred for 6hours. After the filtration of the solvent, 10 mL of methanol was added to the resulting residue, and the mixture was stirred for 2 hours with ice cooling. After the filtration of the solvent, the resulting solid was dried to give 1.59 g of 3',5'-O-bis(4-chlorobenzoyl)-5-methyl-2'-deoxycytidine as a light brown solid. Yield 52%.

$^1$H-NMR (400 MHz, DMSO-d$_6$) δ 1.68 (s, 3H), 2.42–2.56 (m, 2H), 4.47–4.50 (m, 1H), 4.54–4.59 (m, 1H), 4.64–4.69 (m, 1H), 5.60–5.64 (m, 1H), 6.31–6.35 (m, 1H), 6.86 (br s, 1H), 7.39 (br s, 2H), 7.59–7.64 (m, 4H), 7.98–8.04 (m, 4H).

IR (KBr) cm$^{-1}$ 3470, 1681, 1488, 1270, 1093, 760.

Reference Example 2

To the suspension of 0.71 g of 3',5'-O-bis(4-chlorobenzoyl)-5-methyl-2'-deoxycytidine in 4 mL of methanol was added 0.7 mL of the solution of sodium hydroxide in methanol (prepared by dissolving 100 mg of sodium hydroxide in 4 mL of methanol), and the mixture was heated at 45° C. for 5 hours with stirring. After cooling, the mixture was neutralized with a solution of hydrogen chloride in methanol, and methanol was evaporated off. After chloroform and water were added to the residue, the layers were separated, and the aqueous layer was washed with chloroform. The aqueous layer was concentrated and acidified with 6N aqueous hydrogen chloride solution, and after the addition of 5 mL of acetone, allowed to stand overnight at −14° C. The precipitated solid was filtered and dried to give 0.37 g of 5-methyl-2'-deoxycytidine hydrochloride as a light brown solid. Yield 97%.

Reference Example 3

To the solution of 1.01 g of 2'-O-methyluridine and 0.67 g of imidazole in 20 mL of DMF was added 1.3 g of chloro (t-butyl) dimethylsilane, and the resulting mixture was stirred at room temperature for 7 hours. After the completion of the reaction, the reaction mixture was concentrated, and the residue was purified by silica gel chromatography (ethyl acetate:n-hexane =3:7) to give 1.44 g of 3', 5'-O-bis(t-butyldimethylsilyl)-2'-O-methyluridine as a colorless powder. Yield 76%.

$^1$H-NMR (400 MHz, DMSO-d$_6$) δ 0.085 (s, 3H), 0.10 (s, 3H), 0.12 (s, 3H), 0.13 (s, 3H), 0.91 (s, 9H), 0.94 (s, 9H), 3.55 (s, 3H), 3.60 (dd, J=1.7 & 4.9 Hz, 1H), 3.77 (dd, J=2.0 & 12.0 Hz, 1H), 4.18 (dd, J=2.0 & 12.0 Hz, 1H), 4.02–4.06 (m, 1H), 4.24 (dd, J=4.9 & 7.1 Hz, 1H), 5.68 (dd, J=2.0 & 8.3 Hz, 1H), 5.94 (d, J=2.0 Hz, 1H), 8.07 (d, J=8.3 Hz, 1H), 8.77 (br s, 1H).

IR (KBr) cm$^{-1}$ 3463, 2953, 2930, 2858, 1691, 1630, 1542, 1463, 1192, 1124, 1035, 1012, 839, 683.

Example 6

To the solution of 750 mg of 3',5'-O-bis (t-butyldimethylsilyl)-2'-O-methyl uridine in 10 mL of acetonitrile was added 0.23 mL (1.2 times moles based on the uridine derivative) of 1-methylpiperidine and 0.45 mL of triethylamine, and the mixture was cooled. The solution of 614 mg of p-toluenesulfonyl chloride in 5 ml of acetonitrile was added dropwise with ice cooling, and the mixture was stirred for 1 hour. After the disappearance of the starting material, an 1 mL aliquot of the reaction solution was concentrated, and the residue was triturated with ether to remove the precipitated crystals by filtration. The filtrate was concentrated, and the residue was then washed with n-hexane and dried to give [[3,5-O-bis(t-butyldimethylsilyl)-2-O-methylribofuranos-1-yl]-2-oxo-1,2-dihydro-4-pyrimidinyl]-1-methylpiperidinium chloride (a reaction intermediate):

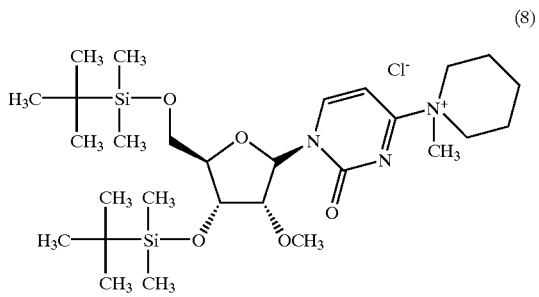

(8)

as a pale yellow oil.

$^1$H-NMR (400 MHz, DMSO-$d_6$) δ 0.065 (s, 3H), 0.088 (s, 3H), 0.095 (s, 3H), 0.10 (s, 3H), 0.89 (s, 18H), 2.2–1.6 (m, 6H), 3.65 (s, 3H), 3.69 (s, 3H), 3.74 (d, J=4.4 Hz, 1H), 3.80 (d, J=12.0 Hz, 1H), 4.0–4.2 (m, 5H), 4.60 (m, 2H), 5.92 (s, 1H), 7.40 (d, J=7.3 Hz, 1H), 8.88 (d, J=7.3 Hz, 1H).

IR (KBr) cm$^{-1}$ 3453, 3194, 3058, 2953, 2930, 2859, 1702, 1462, 1256, 1129, 1073, 838, 780.

To the remaining reaction solution was added 3.5 mL of 28% ammonia water, and the mixture was stirred for 2 hours. The reaction solution was concentrated, diluted with ethyl acetate and washed with water and saturated aqueous sodium chloride solution. The organic layer was dried over magnesium sulfate and concentrated, and the residue was purified by silica gel chromatography (methanol:chloroform=1:25) to give 544 mg of 3',5'-O-bis(t-butyldimethylsilyl)-2'-O-methylcytidine as a colorless powder. Yield 73%.

$^1$H-NMR (400 MHz, DMSO-$d_6$) δ 0.054 (s, 3H), 0.076 (s, 3H), 0.11 (s, 3H), 0.13 (s, 3H), 0.89 (S, 9H), 0.94 (s, 9H), 3.61 (d, J=4.9 Hz, 1H), 3.64 (s, 3H), 3.78 (d, J=12.0 Hz, 1H), 4.04 (d, J=9.0 Hz, 1H), 4.09 (d, J=12.0 Hz, 1H), 4.18 (dd, J=4.9 & 8.8 Hz, 1H), 5.61 (d, J=7.3 Hz, 1H), 5.93 (s, 1H), 8.17 (d, J=7.3 Hz, 1H).

IR (KBr) cm$^{-1}$ 3355, 3200, 2955, 2930, 2859, 1647, 1491, 1125, 1129, 1073, 838, 781.

We claim:

1. A method, characterized in that a uridine derivative represented by formula (1):

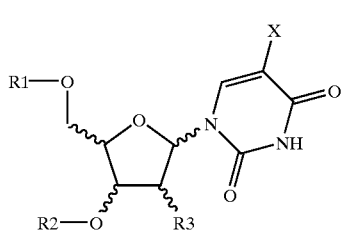

(1)

wherein, X represents a hydrogen atom, a halogen atom, an alkyl group having 1 to 4 carbon atoms, an alkyl group having 1 to 4 carbon atoms substituted with at least one halogen atom, or an alkenyl group having 2 to 4 carbon atoms, and R1 and R2 each independently represent either a hydrogen atom or a hydroxyl-protecting group, and R3 represents a hydrogen atom, a halogen atom, a hydroxyl group, an alkyl group having 1 to 4 carbon atoms, a cyano group, an alkenyl group, an alkynyl group, an alkoxy group having 1 to 4 carbon atoms or a protected hydroxyl group, is reacted with an alicyclic amine represented by formula (4):

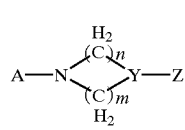

(4)

wherein, n and m each independently represent an integer of 1 to 4, Y represents a methylene group, oxygen atom, sulfur atom or an alkylamine having 1 to 4 carbon atoms provided that, when Y is a methylene group or an alkylamine having 1 to 4 carbon atoms, a carbon atom of either the methylene group or the alkylamine having 1 to 4 carbons atoms may be attached to A to form a ring, A represents an alkyl group having 1 to 4 carbon atoms, an alkyl group having 1 to 4 carbon atoms substituted with at least one halogen atom, an alkenyl group having 2 to 4 carbon atoms, or A attached to Y may form a ring, or salts thereof, and dehydrating reactant, followed by reaction with ammonia, or a primary or a secondary amine represented by formula (2):

HNR4R5 (2)

wherein, R4 and R5 each independently represent a hydrogen atom, an alkyl group having 1 to 4 carbon atoms, a cycloalkyl group having 5 to 8 carbon atoms, an alkyl group having 1 to 4 carbon atoms substituted with at least one halogen atom, or an alkenyl group having 2 to 4 carbon atoms, or R4 and R5 linked together may form a ring, for producing a cytidine derivative represented by formula (3):

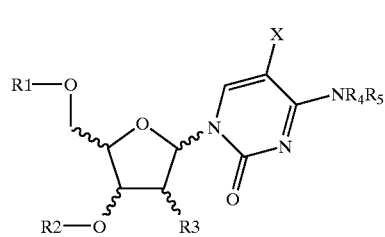

(3)

2. The method for producing cytidine derivatives according to claim 1, where R1 and R2 each independently are an aliphatic acyl group having 1 to 4 carbon atoms, an aromatic acyl group, an aromatic acyl group substituted with at least one alkyl group having 1 to 4 carbon atoms, an aromatic acyl group substituted with at least one halogen atom, an aromatic acyl group substituted with at least one alkoxy group having 1 to 4 carbon atoms, or a trialkylsilyl group, R3 is a hydrogen atom, an alkoxy group having 1 to 4 carbon atoms, an aliphatic alkyloxy group having 1 to 4 carbon atoms substituted with at least one alkoxy group having 1 to 4 carbon atoms, an aliphatic acyloxy group having 1 to 4 carbon atoms, an aromatic acyloxy group, an aromatic acyloxy group substituted with at least one alkyl group having 1 to 4 carbon atoms, an aromatic acyloxy group substituted with at least one halogen atom, or an aromatic acyloxy group substituted with at least one alkoxy group having has 1 to 4 carbon atoms.

3. The method for producing cytidine derivatives according to claim 2, where X represents a hydrogen atom or a methyl group, R3 is a hydrogen atom, a methoxy group, or a methoxyethyloxy group.

4. The method for producing cytidine derivatives according to claim 1, wherein said alicyclic amine is N-methylpiperidine, N-methylmorpholine, 1,4-diazabicyclo[2.2.2]octane, or N, N'-dimethylpiperazine.

5. The method for producing cytidine derivatives according to claim 1, characterized in that said dehydrating reactant is acid halides or acid anhydrides, and said reaction is carried out in the presence of a deacidifying agent.

6. The method for producing cytidine derivatives according to claim 5, wherein said dehydrating reactant is p-toluenesulfonyl chloride.

7. The method for producing cytidine derivatives according to claim 1, wherein the molar ratio of said alicyclic amine to said uridine derivative represented by formula (1) is 1.2 or less.

8. The method for producing cytidine derivatives according to claim 1, characterized in that a reaction intermediate, in reacting uridine derivatives with an alicyclic amine and a dehydrating reactant, is a cytidine derivative represented by formula (5):

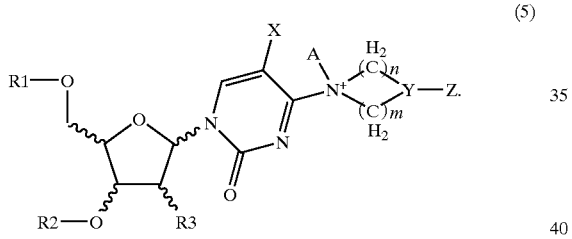

(5)

9. A cytidine derivative represented by formula (5):

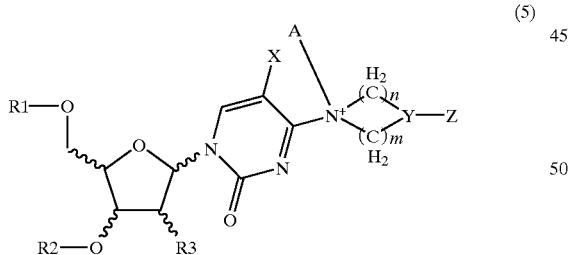

(5)

wherein, X represents a hydrogen atom, a halogen atom, an alkyl group having 1 to 4 carbon atoms, an alkyl group having 1 to 4 carbon atoms substituted with at least one halogen atom, or an alkenyl group having 2 to 4 carbon atoms, R1 and R2 each independently represent either a hydrogen atom or a hydroxyl-protecting group, R3 represents a hydrogen atom, a halogen atom, a hydroxyl group, an alkyl group having 1 to 4 carbon atoms, a cyano group, an alkenyl group, an alkynyl group, an alkoxy group having 1 to 4 carbon atoms, a protected hydroxyl group, n and m each independently represent an integer of 1 to 4, Y represents a methylene group, oxygen atom, sulfur atom or an alkylamine having 1 to 4 carbon atoms provided that, when Y is a methylene group or an alkylamine having 1 to 4 carbon atoms, a carbon atom of either the methylene group of the alkylamine having 1 to 4 carbons atoms may be attached to A to form a ring, A represents an alkyl group having 1 to 4 carbon atoms, an alkyl group having 1 to 4 carbon atoms substituted with at least one halogen atom, an alkenyl group having 2 to 4 carbon atoms, or A attached to Y may form a ring, or salts thereof.

10. The cytidine derivative or salts thereof according to claim 9, wherein X represents a hydrogen atom or a methyl group, R1 and R2 are a hydrogen atom or a hydroxyl-protecting group, R3 is a hydrogen atom, a methoxy group, or a methoxyethyloxy group, n and m are 2, A is a methyl group, and Y is a methylene group or an oxygen atom.

11. A method for producing a cytidine derivative represented by formula (3):

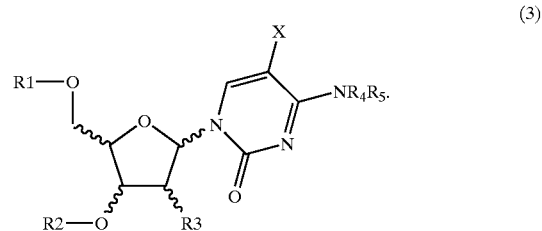

(3)

wherein, X represents a hydrogen atom, a halogen atom, an alkyl group having 1 to 4 carbon atoms, an alkyl group having 1 to 4 carbon atoms substituted with at least one halogen atom, or an alkenyl group having 2 to 4 carbon atoms, R1 and R2 each independently represent either a hydrogen atom or a hydroxyl-protecting group, and R3 represents a hydrogen atom, a halogen atom, a hydroxyl group, an alkyl group having 1 to 4 carbon atoms, a cyano group, an alkenyl group, an alkynyl group, an alkoxy group having 1 to 4 carbon atoms, or a protected hydroxyl group, and R4 and R5 each independently represent a hydrogen atom, an alkyl group having 1 to 4 carbon atoms, a cycloalkyl group having 5 to 8 carbon atoms, an alkyl group having 1 to 4 carbon atoms substituted with at least one halogen atom, or an alkenyl group having 2 to 4 carbon atoms, or R4 and R5 linked together may form a ring, characterized in that the cytidine derivative or salts thereof according to claim 9 is reacted with ammonia or a primary or secondary amine.

* * * * *